(12) United States Patent
Frenkel

(10) Patent No.: US 9,580,574 B2
(45) Date of Patent: Feb. 28, 2017

(54) BIO-BASED BIOCIDE COMPOSITIONS AND METHODS OF PRESERVING THEREWITH

(71) Applicant: Galata Chemicals LLC, Southbury, CT (US)

(72) Inventor: Peter Frenkel, Danbury, CT (US)

(73) Assignee: Galata Chemicals LLC, Southbury, CT (US)

( * ) Notice: Subject to any disclaimer, the term of this patent is extended or adjusted under 35 U.S.C. 154(b) by 0 days.

(21) Appl. No.: 14/443,973

(22) PCT Filed: Dec. 12, 2012

(86) PCT No.: PCT/US2012/069300
§ 371 (c)(1),
(2) Date: May 19, 2015

(87) PCT Pub. No.: WO2014/092704
PCT Pub. Date: Jun. 19, 2014

(65) Prior Publication Data
US 2015/0315359 A1    Nov. 5, 2015

(51) Int. Cl.
*A01N 53/00* (2006.01)
*C08K 5/098* (2006.01)
*C07D 303/16* (2006.01)
*C08K 5/1515* (2006.01)

(52) U.S. Cl.
CPC .......... *C08K 5/1515* (2013.01); *A01N 53/00* (2013.01); *C07D 303/16* (2013.01); *C08K 5/098* (2013.01)

(58) Field of Classification Search
None
See application file for complete search history.

(56) References Cited

U.S. PATENT DOCUMENTS

| | | | | |
|---|---|---|---|---|
| 2,867,594 A * | 1/1959 | Hansen et al. | .......... | C08K 5/526 524/114 |
| 2,978,463 A | 4/1961 | Kuester et al. | | |
| 4,728,540 A | 3/1988 | Gasman | | |
| 5,236,972 A | 8/1993 | Reinhart | | |
| 5,358,979 A | 10/1994 | Van Hoboken et al. | | |
| 5,447,963 A * | 9/1995 | Pcolinsky | .......... | B01D 53/1487 521/114 |
| 5,585,407 A | 12/1996 | Patel et al. | | |
| 5,726,216 A * | 3/1998 | Janke | .......... | C08G 59/38 522/129 |
| 6,743,883 B1 * | 6/2004 | Frances | .......... | A61K 6/0017 106/35 |
| 7,202,287 B2 * | 4/2007 | Cornish | .......... | A01N 47/44 523/122 |
| 2003/0187095 A1 * | 10/2003 | Cornish | .......... | A01N 47/44 523/122 |
| 2006/0020062 A1 * | 1/2006 | Bloom | .......... | C07D 303/42 524/114 |
| 2007/0286975 A1 * | 12/2007 | Fazel | .......... | C08G 18/0804 428/41.8 |
| 2009/0192265 A1 | 7/2009 | Hasegawa et al. | | |
| 2010/0324185 A1 | 12/2010 | Geng et al. | | |
| 2011/0118374 A1 * | 5/2011 | Schneider | .......... | C08F 2/50 522/25 |
| 2012/0181058 A1 * | 7/2012 | Chaudhary | .......... | C08K 5/0091 174/110 V |
| 2012/0329651 A1 | 12/2012 | Dave et al. | | |
| 2014/0336086 A1 * | 11/2014 | Frenkel | .......... | C09K 8/035 507/136 |

FOREIGN PATENT DOCUMENTS

JP    11349415    12/1999

OTHER PUBLICATIONS

Irganox 1010, Aug. 98.*
Doll et al "Emulsification of Chemically Modified Vegetable Oils for Lubricant Use" Journal of Surfactants and Detergenets [online], Dec. 27, 2010, vol. 14, pp. 131-138. http://naldc.nal.usda.gov/download/147782/PDF.
Cappitelli et al. "Microorganisms Attack Synthetic Polymers in Items Representing Our Cultural Heritage" Applied and Environmental Microbiology [online] Dec. 7, 2007, vol. 74, Iss. 3, pp. 564-569 http://www.ncbi.nim.nih.gov/pmc/articles/PMC2227722.
Search Report and Written Opinion mailed in PCT/US12/69300 on Feb. 26, 2013.

* cited by examiner

Primary Examiner — Peter A Salamon
(74) Attorney, Agent, or Firm — Dilworth IP, LLC

(57) ABSTRACT

Bio-based biocide compositions containing epoxidized 2-ethylhexyl soyate and a solvent such as epoxidized soybean oil are disclosed. When incorporated into polymers such as PVC, preserved polymer compositions result. The invention also provides methods for preserving polymers, including incorporating these compositions into PVC in accordance with these methods.

24 Claims, No Drawings

BIO-BASED BIOCIDE COMPOSITIONS AND METHODS OF PRESERVING THEREWITH

FIELD OF THE INVENTION

The invention relates to methods of preserving polymers and other industrial products comprising incorporating into said polymers and other industrial products bio-based biocide compositions, as additives for reducing microbial growth. The invention further relates to bio-based biocide compositions comprising epoxidized 2-ethylhexyl soyate and at least one solvent, said compositions being suitable as industrial preservatives for protecting polymers, including halogenated polymers such as polyvinyl chloride, and other industrial products from microbial growth.

BACKGROUND OF THE INVENTION

Biocidal products are used in numerous areas, such as for controlling growth of bacteria, fungi, and algae, for example. Without biocides, microbes can develop spores and grow on the surface of polymeric materials or spoil industrial products, resulting in allergic reactions, unpleasant odors, staining, discoloration, and loss of physical properties to name a few. The latter is known to lead to premature product failure.

Use of biocides in polyvinyl chloride (PVC) and other synthetic polymers is commonly directed to either protection of the susceptible polymer material from attack by microorganisms and/or achievement of biocidal surfaces. Polymer so protected, i.e., by incorporation of biocides, is known in the art as preserved polymer.

It is well-established that certain plastic materials like flexible PVC, polyurethanes or silicone may be easily attacked by microorganisms leading to discoloration or mechanical failure (R. Borgmann-Strahsen, *Microbiocides for PVC and Other Polymers*, in Industrial Biocides—Selection and Application, Royal Society of Chemistry, 2002, pg. 103-107, ed. D. R. Karsa and D. Ashworth). The susceptibility to microbial attack is mainly attributed to the plasticizer content of the plastic materials, as well as other additives such as stabilizers and antioxidants. The predominant organisms on the surface of those plastics are fungi and actinomycetes.

Due to the propensity of microorganisms to attack and/or consume plasticizers, the primary use of most organic biocides as additives for plastics is as fungicides (fungistats) in flexible or semi-flexible PVC. Such consumption of PVC plasticizers may lead to mechanical failure due to embrittlement, discoloration and malodor.

In terms of their susceptibility to microbial attack, these plasticizers can be grouped as follows: highly susceptible types, moderately susceptible types and low susceptible types. Highly susceptible plasticizers include sebacates, epoxidized oils, polyesters, and glycolates (see also a Ochs, *Antimicrobials*, in: *Plastics Additives Handbook*, 5$^{th}$ edition, pg. 647-680; editor: Hans Zweifel; Hanser Publishers, Munich, 2001). Among the moderately susceptible plasticizers are adipates and azelates while the group of low susceptible plasticizers is comprised of phthalates, phosphates, and chlorinated hydrocarbons.

Selected biocides, e.g. fungicides, that are used to protect plastic materials against attack from microorganisms include 10,10'-oxybisphenoxarsine (OPBA), 4,5-dichloro-2-n-octyl-4-isothiazolin-3-one (DCOIT), 2-n-octyl-4-isothiazolin-3-one (OIT), n-butyl-1,2-benzisothiazolin-3-one (BBIT), 2,4,4'-trichloro-2'-hydroxy-diphenyl-ether (TCPP), 3-iodo-2-propynyl butyl carbamate (IPBC), N-(tricholomethylthio phthalamide), zinc pyrithione (ZNP), 2-(4-thiazolyl)-benzimidazol (TBZ), carbendazim and 3-benzo[b]thien-2-yl-5,6-dihydro-1,4,2-oxathiazine 4-oxide (cf. Townsend Solutions, *Townsend's Eighth Report on the Global Plastics Additives Market*, Houston, Tex., 2012).

Several commercially available organic biocides are formulated and supplied in a plasticizer carrier. For example, OIT is supplied at varying concentrations in dioctylphthalate, diisononylphthalate, epoxidized soybean oil, and diisodecylphthalate (a more complete listing is provided at D. Ochs, *Antimicrobials*, in: *Plastics Additives Handbook*, 5$^{th}$ edition, pg. 647-680; editor: Hans Zweifel; Hanser Publishers, Munich, 2001).

Several patents and patent applications relate to organic biocides and plasticizers, as referred to hereinbelow.

U.S. Pat. No. 4,728,540 describes a process for introducing into already manufactured and fabricated vinyl products special function additives which impart to the vinyl product some useful property which it did not possess before as, for example, UV resistance, mildew resistance, etc. The process involves the use of vinyl plasticizers in which the additives are readily soluble to convey the additives into already manufactured and fabricated vinyl plastic products. Special function additives include UV stabilizers, mildewcides, fragrances, fungicides, antifogging agents, biocides, disinfectants, lubricants, antioxidants, water repellents, thickeners, surfactants, bacteriacides, vinyl heat stabilizers, antistats, release agents, anti blocking agents and the like.

U.S. Pat. No. 5,236,972 describes a thermoplastic powder slurry for making fiber reinforced composite structure prepregs having tack, drape and easy handleability. A slurry of thermoplastic resin powder suspended in a solution of distilled water, a water-soluble polymer, a wetting agent, a biocide, a plasticizer and an antifoamer, which is used to impregnate suitable reinforcing fibers, either continuous or woven, makes a prepreg having tack, drape and easy handleability.

U.S. Pat. No. 5,358,979 discloses a microbiocide-containing concentrate for use in thermoplastic polymers as well as in plastisols. The concentrate is primarily solid at ambient conditions and comprises from 1-30 wt % of a microbiocide, a polymer plasticizer and up to 20 wt % of a thermoplastic resin. These concentrates are primarily useful as masterbatch compositions used for incorporation into polymers in order to protect said polymers from fungal or bacterial attack. Also disclosed are processes for incorporating these materials into a polymer or plastisol, and polymers or plastisols made by these processes.

U.S. Pat. No. 5,585,407 relates to water-based coatable compositions for application to a substrate to inhibit the growth of microbes for extended periods of time, durable removable biocidal polymeric coatings resulting from such coatable compositions, a method of protecting a substrate from the growth of microbes and substrates resistant to such growth. The coatable compositions comprise an acrylate emulsion polymer comprising the reaction product of one or more acrylate or methacrylate monomers and one or more carboxylic acid monomers, an organoalkoxysilane, an effective amount of biocide, plasticizer and water.

Japanese Patent No. 11349415 (Abstract) discloses industrial biocide compositions containing epoxidized soybean oil as a diluent.

Notwithstanding the above literature, there is a continuing need for improved biocides such as bio-based biocides derived from natural resources.

SUMMARY OF THE INVENTION

In one aspect, the invention is directed to a method of preserving a polymer comprising: combining a polymer and, in an amount effective for preservation, a bio-based biocide composition comprising epoxidized 2-ethylhexyl soyate and at least one solvent to provide a preserved polymer composition.

DETAILED DESCRIPTION OF THE INVENTION

The present invention relates to bio-based biocide compositions for industrial applications. In some embodiments, the bio-based biocide compositions of the invention comprise, as biocidal component, epoxidized 2-ethylhexyl soyate and at least one solvent. The inventive compositions are suitable as industrial preservatives for protecting and preserving polymers, including halogenated polymers, for example, polyvinyl chloride, and other industrial products. The invention further relates to a method of preserving these polymers and other industrial products, said method comprising incorporation, for example by addition, of the bio-based biocide compositions into said polymers and other industrial products.

Representative solvents are epoxidized vegetable oils, esters, epoxidized esters, phthalates, alcohols ketones and alkylpyrrolidones, alkyl phosphates, and mixtures of any two or more thereof. Preferable solvents include epoxidized vegetable oils, for example, epoxidized soybean oil and epoxidized linseed oil. In one embodiment, the solvents act as diluent for epoxidized 2-ethylhexyl soyate.

In one embodiment, the bio-based biocide compositions of the invention comprise epoxidized 2-ethylhexyl soyate and epoxidized soybean oil.

In other embodiments, the bio-based biocide compositions of the invention reduce, suppress, and/or prevent microbial growth, that is, growth of microorganisms. When exposed to fungi, the bio-based compositions of the invention display resistance to fungi.

In some embodiments, the bio-based biocide compositions according to the invention are incorporated into polymers to provide preserved polymer compositions. When incorporated into polymers, the bio-based biocide compositions reduce, suppress, and/or prevent microbial growth on the polymers. In some such embodiment, these compositions achieve biocidal surfaces on the polymers.

The preserved polymer compositions of the invention, upon exposure to fungi, exhibit resistance to fungi.

In other embodiments, the preserved polymer compositions having incorporated therein the bio-based biocide compositions of the invention exhibit improved resistance to fungi, as compared to the resistance to fungi of an otherwise identical composition except for the presence of the bio-based biocide compositions. Resistance to fungi is improved by, for example, at least 15%. Other examples of improved resistance to fungi include: by at least 20%, 30%, 40%, 50%, 60% and 70%, as compared to the resistance to fungi of an otherwise identical composition except for the presence of the bio-based biocide compositions. Generally, resistance to fungi may be improved in the range from at least 15 to 70%.

Aforementioned resistance to fungi, including improvement of resistance, is observed by any of the known test methods for assessing antimicrobial efficacy of the preserved polymer compositions, in accordance with the invention. Representative test methods include Agar Plate Tests, Direct Contamination Tests and In-use tests. Further examples of suitable test methods are EN ISO 846, ASTM G21-90 and ASTM G21-96.

Representative fungi include *Aspergillus niger, Aureobasidium pullulans, Aspergillus terreus, Candida albicans, Chaetomium globosum, Gliocladium virens, Paecilomyces variotti, Penicillium funiculosum, Penicillium pinophilum, Penicillium ochrochloron, Scopulariopsis brevicaulis, Trichoderma viride, Trichophyton mentagrophytes*, and the like.

In further embodiments, the bio-based biocide compositions of the invention comprise blends containing epoxidized 2-ethylhexyl soyate and solvents such as epoxidized soybean oil. These blends are stable, homogeneous, and liquid in appearance.

Any of the known blending processes, methods and techniques, for example, admixing and mixing, can be used to prepare these liquid blends for the purpose of attaining homogeneity and/or stability. In some embodiments, epoxidized 2-ethylhexyl soyate and solvent are combined and kept—with or without agitation—for a predetermined amount of time at ambient temperature. In one embodiment, the predetermined amount of time is in the range of from 1 to 24 hours. Preferred are from 1 to 10 hours, more preferred from two to four hours. Also preferred are times of 1, 2, 3, 4, 5, 6, 7, 8, 9, 10, 12, 14, 18, 22 hours.

In one embodiment still, epoxidized 2-ethylhexyl soyate and solvent are combined at a temperature in the range of from 0-300° C. Preferred is a temperature range of from 0-250° C., 10-300° C., 10-200° C., 10-100° C., more preferred is from 20-80° C., 30-60° C.

In one embodiment, the ratio of epoxidized 2-ethylhexyl soyate to solvent is in the range of from about 5 to about 99.99 weight percent, based on total weight of epoxidized 2-ethylhexyl soyate and solvent. Preferred is a ratio in the range of from 20 to 90 weight percent, more preferably in the range from about 40 to about 60 weight percent. The ratio of epoxidized 2-ethylhexyl soyate and solvent can also be in the range of from about 10 to 90, 20 to 80, 30 to 70 and 40 to 60 weight percent, based on total weight of the components. The ratio of epoxidized 2-ethylhexyl soyate to solvent can further be from about 5 to about 99, 10-99, 20-99, 30-99, 40-99, 50-99 and from about 60 to about 99 weight percent, based on total weight of the composition.

As provided above, the inventive bio-based biocide compositions are incorporated into polymers and other industrial products, mainly for preserving these materials. Generally, such incorporation occurs in an amount effective for the preservation of the polymers and other industrial products.

Preferably, the bio-based biocide compositions are incorporated into polymers in the range of from about 1 to about 200 parts, based on 100 parts polymer. More preferable is a range from between about 2 to about 150 parts, from about 5 to about 100 parts, from about 5 to about 80 parts, from about 10 to about 60 parts, from about 20 to about 50 parts, and from about 30 to about 50 parts, based on 100 parts polymer. These ranges represent examples of effective amounts. Other examples of effective amounts include about 1, 2, 5, 10, 20, 30, 36, 40, 50, 60, 80, 100 parts, based on 100 parts polymer.

Examples of polymers include non-halogenated polymers and halogenated polymers. Exemplary non-halogenated polymers are olefins, thermoplastic polyurethanes (TPU), acrylates, ABS, MBS, NBR, SAN, EVA, CPE, PMA, PMMA, EPDM, latex, and wood-plastic composites thereof. These abbreviations are familiar to those skilled in the art and have the following meanings: ABS: acrylonitrile-butadiene-styrene; SAN: styrene-acrylonitrile; NBR: acrylonitrile-butadiene; EVA: ethylene-vinyl acetate; MBS: methacrylate-butadiene-styrene; PMA: poly(methyl acrylate); PMMA: poly(methyl methacrylate), CPE: chlorinated polyethylene; and EPDM: ethylene propylene diene monomer. Other possible polymers are in particular styrene-acrylonitrile copolymers based on acrylate (ASA).

Examples of halogenated polymers include polymers of vinyl chloride (PVC), of vinylidene chloride, vinyl resins whose structure contains vinyl chloride units, such as copolymers of vinyl chloride and alkylglycidyl acrylates, copolymers of vinyl chloride and vinyl esters of aliphatic acids, in particular vinyl acetate, copolymers of vinyl chloride with esters of acrylic or methacrylic acid and with acrylonitrile, copolymers of vinyl chloride with diene compounds and with unsaturated dicarboxylic acids or anhydrides of these, such as copolymers of vinyl chloride with diethyl maleate, diethyl fumarate or maleic anhydride, postchlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and copolymers of the same with vinyl chloride and with other polymerizable compounds; polymers of vinyl chloroacetate and of dichlorodivinyl ether; chlorinated polymers of vinyl acetate, chlorinated polymeric esters of acrylic acid and of α-substituted acrylic acid; polymers of chlorinated styrenes, such as dichlorostyrene; chlorinated rubbers; chlorinated polymers of ethylene; polymers and postchlorinated polymers of chlorobutadiene and copolymers of these with vinyl chloride, chlorinated natural or synthetic rubbers, and also mixtures of the polymers mentioned with themselves or with other polymerizable compounds. For the purposes of this invention, PVC includes copolymers with polymerizable compounds, such as acrylonitrile, vinyl acetate or ABS, where these may be suspension polymers, bulk polymers or else emulsion polymers.

Preference is given to a PVC homopolymer, postchlorinated PVC (C-PVC), also in combination with polyacrylates.

Other suitable polymers are graft polymers of PVC with EVA, ABS or MBS. Preferred substrates are mixtures of the abovementioned homo- and copolymers, in particular vinyl chloride homopolymers, with other thermoplastic or/and elastomeric polymers, in particular blends with ABS, MBS, NBR, SAN, EVA, CPE, MBAS, PMA, PMMA, EPDM or with polylactones, in particular from the group consisting of ABS, NBR, NAR, SAN and EVA. Also included are wood-plastic composites comprising PVC.

Examples of other suitable industrial products are paints, inks, coatings, metalworking fluids, paper, wood, disinfectants, textiles, products for use in personal care, households, cleaners, and water treatment applications.

In one embodiment, the bio-based biocide compositions of the invention are incorporated into halogenated polymers, for example PVC, in combination with conventional plasticizers. Conventional plasticizers are known in the art.

Exemplary conventional plasticizers are phthalates, hydrogenated phthalates, aliphatic esters of dicarboxylic acids, polymeric esters of dicarboxylic acids, citrates, sucrose esters, levulinic ketal esters, phosphates, alkyl phenol sulfonates, pyrrolidones, and the like, and mixtures of two or more thereof. Preferable are phthalates, substantially fully esterified mono-, di- and tribasic acids, adipates, azelates, succinates, glutarates, glycol esters, sucrose esters, levulinic ketal esters, citrates, phosphates, alkyl phenol sulfonates and mixtures of at least two thereof. An overview of conventional plasticizers is found at PLASTICS ADDITIVES HANDBOOK, 4$^{th}$ edition, ed. Gächter/Müller, Hansa Gardner Publishers, Munich, 1993, pg. 327-422, which is incorporated herein by reference in its entirety.

Suitable examples of conventional plasticizers, used in accordance with the invention in combination with the inventive bio-based biocide compositions, also include those from the following groups and mixtures thereof:

A. Phthalate Plasticizers. Exemplary materials preferably include di-2-ethylhexyl, diisononyl and diisodecyl phthalate, also known by the common abbreviations DOP (dioctyl phthalate, di-2-ethylhexyl phthalate), DINP (diisononyl phthalate), and DIDP (diisodecyl phthalate).

B. Aliphatic Ester Plasticizers. Examples include esters of aliphatic dicarboxylic acids, in particular esters of adipic, azelaic or sebacic acid; preferably di-2-ethylhexyl adipate and diisooctyl adipate and esters of trimellitic acid, such as tri-2-ethylhexyl trimellitate, triisodecyl trimellitate (mixture), triisotridecyl trimellitate, triisooctyl trimellitate (mixture), and also tri-$C_6$-$C_8$-alkyl, tri-$C_7$-$C_9$-alkyl and tri-$C_9$-$C_{11}$-alkyl trimellitate. Common abbreviations are TOTM (trioctyl trimellitate, tri-2-ethylhexyl trimellitate), TIDTM (triisodecyl trimellitate) and TITDTM (triisotridecyl trimellitate). Other examples include glutarates, malonates, oxalates, suberates, and glycolates.

C. Polymeric Plasticizers. Common starting materials for preparing polyester plasticizers include dicarboxylic acids, such as adipic, phthalic, azelaic or sebacic acid; diols, such as 1,2-propanediol, 1,3-butanediol, 1,4-butanediol, 1,6-hexanediol, neopentyl glycol and diethylene glycol.

D. Citric Acid Ester Plasticizers. A definition of these and other plasticizers and examples of the same are given in "Kunststoffadditive" ["Plastics Additives"], R. Gächter/H. Müller, Carl Hanser Verlag, 3rd Ed., 1989, Chapter 5.9.6, pp. 412-415, and in "PVC Technology", W. V. Titow, 4th Ed., Elsevier Publ., 1984, pp. 165-170, each of which is herein incorporated by reference in its entirety.

E. Epoxy Compound Plasticizers. Exemplary materials include epoxidized polybutadiene and polyisoprene, if desired also in a partially hydroxylated form, or of glycidyl acrylate and glycidyl methacrylate as homo- or copolymer. Also included as examples are epoxidized vegetable oils, such as epoxidized soybean oil and epoxidized linseed oil, epoxidized $C_1$-$C_8$ alkyl soyates, epoxidized $C_1$-$C_8$ alkyl tallates, and the like.

In other embodiments, the bio-based biocide compositions provided by the invention are incorporated into PVC and PVC articles, including flexible and semi-flexible PVC and PVC articles. These materials, when tested for Shore A Hardness, exhibit Shore A Hardness data similar to identical materials except for the presence of the bio-based biocide compositions of the invention. Those skilled in the art can understand Shore A Hardness to be a measure of the hardness of a material, commonly measured on a Durometer in accordance with a defined test method, for example ASTM D2240.

The bio-based biocide compositions of the invention can be incorporated into PVC in combination with PVC stabilizers. PVC stabilizes are known in the art (see for example *Plastics Additives Handbook*, 5$^{th}$ Edition, ed. Hans Zweifel, Hanser Publishers. Munich, 2001, pg. 427-483, which is incorporated herein by reference in its entirety). Exemplary PVC stabilizers include zinc intermediates, such as zinc salts, zinc acetylacetonate, liquid phosphite esters, metal perchlorates and the like.

In some embodiments of the invention, the inventive bio-based biocide compositions also include one or more additives to enhance or modify one or more chemical or physical properties, such as heat stability, lubricity, color, viscosity, to name a few. Exemplary additives include, but are not limited to, conventional plasticizers, heat stabilizers, lubricants, viscosity control agents, UV absorbers, antioxidants, antistatic agents, conventional antimicrobials and antifungal compounds (i.e. conventional microbiocides), among other compounds conventionally used in flexible PVC formulations. An overview of these can be found in *Plastics Additives Handbook,* 5*th* edition, editor: Hans Zweifel; Hanser Publishers, Munich, 2001 and *Plastics Additives and Modifiers Handbook*, ed. J. Edenbaum; Van Nostrand Reinhold, 1992, which is incorporated herein by reference in its entirety.

A single additive can serve multiple purposes. For example, a single additive can serve both as heat stabilizer and lubricant. Additives used in combination with the plasticizer compositions of the invention can be incorporated into halogenated polymers, including PVC, in any amount suitable to achieve the desired purpose.

In various embodiments of the invention, use is made of one or more of the following additives and/or mixtures thereof with the plasticizer compositions of the present invention in halogen-containing polymers.

I. Polyols and Other Organic Components

Exemplary compounds of this type include sorbitol, triethanolamine, polyethylene glycols, β-diketones, such as dibenzoylmethane, uracils, and the like. Examples of the amounts of the polyols used are from 0.01 to 20 parts by weight, advantageously from 0.1 to 10 parts by weight and in particular from 0.1 to 5 parts by weight, based on 100 parts by weight of PVC.

II. Hydrotalcite Co-Stabilizers

The chemical composition of these compounds is known to one of ordinary skill in the art (see e.g., DE 3 843 581, U.S. Pat. No. 4,000,100, EP 0 062 813 and WO 93/20135, each of which is herein incorporated by reference in its entirety).

Compounds from the hydrotalcite series may be described by the following general formula

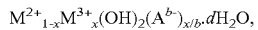

$$M^{2+}{}_{1-x}M^{3+}{}_x(OH)_2(A^{b-})_{x/b} \cdot dH_2O,$$

where $M^{2+}$=one or more of the metals selected from the group consisting of Mg, Ca, Sr, Zn and Sn, $M^{3+}$=Al or B, $A^n$ is an anion of valency n, b is a number from 1-2, 0<x<0.5, and d is a number from 0-20.

Preference is given to compounds with $A''$=$OH^-$, $ClO_4^-$, $HCO_3^-$, $CH_3COO^-$, $C_6H_5COO^-$, $CO_3^{2-}$, $(CHOHCOO)_2^{2-}$, $(CH_2COO)_2^{2-}$, $CH_3CHOHCOO^-$, $HPO_3^-$ or $HPO_4^{2-}$;

Examples of hydrotalcites include $Al_2O_3 \cdot 6MgO \cdot CO_2 \cdot 12H_2O$, $Mg_4 \cdot 5Al_2(OH)_{13} \cdot CO_3 \cdot 3.5H_2O$, $4MgO \cdot Al_2O_3 \cdot CO_2 \cdot 9H_2O$, $4MgO \cdot Al_2O_3 \cdot CO_2 \cdot 6H_2O$, $ZnO \cdot 3MgO \cdot Al_2O_3 \cdot CO_2 \cdot 8-9H_2O$ and $ZnO \cdot 3MgO \cdot Al_2O_3 \cdot CO_2 \cdot 5-6H_2O$.

III. Metal Soap Stabilizers

Metal soaps are primarily metal carboxylates, preferably of relatively long-chain carboxylic acids. Well-known examples of these are stearates, oleates, palmitates, ricinolates, hydroxystearates, dihydroxy-stearates and laurates.

Exemplary metals include alkali, alkaline earth and rare earth metals. Preferred are Na, K, Mg, Ca, Sr, Ba, Pb, Zn, Al, La, and Ce. Use is frequently made of so-called synergistic mixtures, such as barium/zinc stabilizers, magnesium/zinc stabilizers, calcium/zinc stabilizers or calcium/magnesium/zinc stabilizers. The metal soaps may be used either alone or in mixtures. An overview of common metal soaps is found in Ullmann's Encyclopedia of Industrial Chemistry, 5th Ed., Vol. A16 (1985), pp. 361 et seq, which is incorporated herein by reference in its entirety.

The metal soaps or mixtures of these may be used in amounts of, for example, 0.001 to 10 parts by weight, expediently 0.01 to 8 parts by weight, particularly preferably 0.05 to 5 parts by weight, based on 100 parts by weight of PVC.

IV. Alkali Metal and Alkaline Earth Metal Compounds

For the purposes of the present invention, examples of these materials include the carboxylates of the acids described above, but also corresponding oxides or, respectively, hydroxides or carbonates. Mixtures of these with organic acids are also possible. Examples include NaOH, KOH, CaO, Ca(OH)$_2$, MgO, Mg(OH)$_2$, BaO, Ba(OH)$_2$, Sr(OH)$_2$, Al(OH)$_3$, CaCO$_3$ and MgCO$_3$ (and also basic carbonates), and also selected salts of Na and of K, including perchlorates. In the case of alkaline earth carboxylates and Zn carboxylates it is also possible to use adducts of these as so-called "overbased" compounds. In addition to the stabilizers according to the invention it is preferable to use alkali alkaline earth metal carboxylates.

V. Metal Perchlorates

Representative metal perchlorates include alkali metal, alkaline earth metal, aluminum, zinc, lanthanum or cerium metal perchlorates. Preferred are alkali metal perchlorates. More preferred are lithium, sodium and potassium perchlorate. Of particular preference is sodium perchlorate.

In some embodiments, the metal perchlorates are provided as metal perchlorate hydrates, preferably in powder form. Exemplary hydrates are monohydrates, dihydrates, trihydrates and tetrahydrates.

Perchlorate solutions are also commercially available. For example, Galata Chemicals LLC manufactures Mark CE-350, a 2-(2-butoxyethoxy)ethanol solution of sodium perchlorate Preferred are 30 and 60 percent (by. wt.) aqueous sodium perchlorate solutions.

Examples of the amounts of the metal perchlorates used are from about 0.01 to about 10 parts by weight, advantageously from about 0.1 to about 5 parts by weight and in particular from about 0.1 to about 3 parts by weight, based on 100 parts by weight of PVC. Of particular interest is a range from about 0.1 to about 1 parts, based on 100 parts by weight of PVC.

VI. Organotin Stabilizers

Examples of possible compounds of this type include both mono- and dimethyl, butyl and octyltin mercaptides, maleates and the like.

VII. Phosphites (Triesters of Phosphorous Acid)

Organic phosphites are known co-stabilizers for chlorine-containing polymers. Examples of these are triphenyl phosphite, diphenyl isodecyl phosphite, ethylhexyl diphenyl phosphite, phenyl diisodecyl phosphite, trilauryl phosphite, triisononyl phosphite, triisodecyl phosphite, epoxy grade triphenyl phosphite, diphenyl phosphite, and tris(nonylphenyl)phosphite. Advantageous use may also be made of phosphites of various di- or polyols.

Examples of total amounts of the organic phosphites used, or of mixtures thereof, are from 0.01 to 10 parts by weight, advantageously from 0.05 to 5, and in particular from 0.1 to 3 parts by weight, based on 100 parts by weight of PVC.

VIII. Lubricants

Examples of possible lubricants include fatty acids, fatty alcohols, montan wax, fatty acid esters, PE waxes, amide waxes, chloroparaffins, glycerol esters and alkaline earth metal soaps, and fatty ketones, and also the lubricants, or combinations of the lubricants, listed in EP0259783, which is herein incorporated by reference in its entirety. Stearic acid, stearic esters and calcium stearate are preferred.

IX. Fillers

Fillers such as calcium carbonate, dolomite, wollastonite, magnesium oxide, magnesium hydroxide, silicates, china clay, talc, glass fibers, glass beads, wood flour, mica, metal oxides or metal hydroxides, carbon black, graphite, rock flour, heavy spar, glass fibres, talc, kaolin and chalk may be used in accordance with some embodiments of the present invention (see e.g., HANDBOOK OF PVC FORMULATING, E. J. Wickson, John Wiley & Sons, Inc., 1993, pp. 393-449; see also TASCHENBUCH der Kunststoffadditive [Plastics Additives Handbook], R. Gächter & H. Müller, Carl Hanser, 1990, pp. 549-615), each of which is herein incorporated by reference in its entirety.

The fillers may be used in amounts of preferably at least one part by weight, for example 1 to 20 parts by weight, expediently 1 to 10 parts by weight and in particular from 1 to 5 parts by weight, based on 100 parts by weight of PVC.

X. Pigments

Suitable substances are known to those of ordinary skill in the art. Examples of inorganic pigments include $TiO_2$, pigments based on zirconium oxide, $BaSO_4$, and zinc oxide (zinc white). Mixtures of various pigments may also be used. A definition and further descriptions are found in the "Handbook of PVC Formulating", E. J. Wickson, John Wiley & Sons, New York, 1993, which is herein incorporated by reference in its entirety.

XI. Antioxidants

Exemplary embodiments include phenols, alkylated monophenols, e.g., 2,6-di-tert-butyl-4-methylphenol, alkylthiomethylphenols, e.g., 2,4-dioctylthiomethyl-6-tert-butylphenol, alkylated hydroquinones, e.g., 2,6-di-tert-butyl-4-methoxyphenol, hydroxylated thiodiphenyl ethers, e.g., 2,2'-thiobis(6-tert-butyl-4-methylphenol), alkylidenebisphenols, e.g., 2,2'-methylene-bis(6-tert-butyl-4-methylphenol), benzyl compounds, e.g., 3,5,3',5'-tetra-tert-butyl-4,4'-dihydroxydibenzyl ether, hydroxybenzylated malonates, e.g., dioctadecyl 2,2-bis(3,5-di-tert-butyl-2-hydroxybenzyl)malonate, hydroxybenzyl aromatics, e.g., 1,3,5-tris(3,5-di-tert-butyl-4-hydroxybenzyl)-2,4,6-trimethylbenzene, triazine compounds, e.g., 2,4-bisoctylmercapto-6-(3,5-di-tert-butyl-4-hydroxyanilino)-1,3,5-triazine, phosphonates and phosphonites, e.g., dimethyl 2,5-di-tert-butyl-4-hydroxybenzyl-phosphonate, acylaminophenols, e.g., 4-hydroxylauranilide, esters of β-(3,5-ditert-butyl-4-hydroxyphenyl)propionic acid, e.g., pentaerythritol tetrakis(3-(3,5-di-tert-butyl-4-hydroxyphenyl)propionate), octadecyl-3-(3,5-di-tert-butyl-4-hydroxyphenyl)propionate, β-(5-tert-butyl-4-hydroxy-3-methylphenyl)propionic acid, β-(3,5-dicyclohexyl-4-hydroxyphenyl)propionic acid, esters of 3,5-ditert-butyl-4-hydroxyphenylacetic acid with mono- or polyhydric alcohols, amides of β-(3,5-ditert-butyl-4-hydroxyphenyl) propionic acid, such as, for example, N,N'-bis(3,5-ditert-butyl-4-hydroxyphenyl-propionyl)hexamethylenediamine, vitamin E (tocopherol) and derivatives. Mixtures of at least two or more antioxidants may also be used.

Examples of the amounts of the antioxidants used are from about 0.01 to about 10 parts by weight, advantageously from 0.1 to 5 parts by weight and in particular from 0.1 to 3 parts by weight, based on 100 parts by weight of PVC.

XII. UV Absorbers and Light Stabilizers

Examples of UV absorbers and light stabilizers include 2-(2'-hydroxyphenyl)benzotriazoles, such as 2-(2'-hydroxy-5'-methylphenyl)-benzotriazole, 2-hydroxybenzophenones, esters of unsubstituted or substituted benzoic acids, such as 4-tert-butylphenyl salicylate, phenyl salicylate, acrylates, nickel compounds, oxalamides, such as 4,4'-dioctyloxyoxanilide, 2,2'-dioctyloxy-5,5'-ditert-butyloxanilide, 2-(2-hydroxyphenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, sterically hindered amines, such as bis(2,2,6,6-tetramethylpiperidin-4-yl) sebacate, bis(2,2,6,6-tetramethylpiperidin-4-yl) succinate and the like. Mixtures of any two or more of the UV absorbers and/or light stabilizers may also be used.

XIII. Conventional Microbiocides

Exemplary conventional microbiocides include 10,10'-oxybisphenoxarsine (OPBA), 4,5-dichloro-2-n-octyl-4-isothiazolin-3-one (DCOIT), 2-n-octyl-4-isothiazolin-3-one (OIT), n-butyl-1,2-benzisothiazolin-3-one (BBIT), 2,4,4'-trichloro-2'-hydroxy-diphenyl-ether (TCPP), 3-iodo-2-propynyl butyl carbamate (IPBC), N-(tricholomethylthio phthalamide), zinc pyrithione (ZNP), 2-(4-thiazolyl)-benzimidazol (TBZ), carbendazim and 3-benzo[b]thien-2-yl-5,6-dihydro-1,4,2-oxathiazine 4-oxide, 2,3,5,6 tetrachloro 4 (methyl sulfanyl)pyridine, N-trichloromethyl-thio-4-cyclohexene-1,2-dicarboximide, octhilinone, pentachlorophenyl laurate, tetrachloroisophthalonitrile, silver-zinc zeolite, silver-copper zeolite, and the like. Mixtures of two or more conventional microbiocides are also used. A definition and further descriptions are found at D. Ochs, *Antimicrobials, in: Plastics Additives Handbook, 5$^{th}$ edition*, pg. 647-680; editor: Hans Zweifel; Hanser Publishers, Munich, 2001, which is incorporated herein by reference in its entirety.

As provided above, the bio-based biocide compositions according to the invention are useful for the protection and preservation of polymers and other industrial products, in particular flexible PVC formulations and PVC articles, by preventing, reducing or suppressing microbial growth. Those skilled in the art will recognize that polymers and other industrial products may be susceptible to attack by microorganisms, leading to undesirable loss of original properties of these materials. Said original properties include mechanical properties such as tensile strength and flexibility, color and odor.

Examples of their use include PVC wire and cable jacketing and insulation, pool liners, decorative sheeting, roofing membranes, films including agricultural and packaging films, hoses such as garden hoses, tubing, floorcovering, shower curtains, carpet backing, interior and exterior trim, outdoor furniture, sealants and coatings, gaskets, inks, toys, and automotive parts. Additional examples of the use of the inventive compositions include plastisols, for example, plastisol for artificial leather, PVC floorings, textile coatings, wall coverings, boat and automotive coverings, coil coatings, carpet backing, floor mats for motor vehicles, wood-PVC plastic composites and adhesives.

In some embodiments still, the invention provides a method of preserving a polymer comprising (i) providing the polymer and (ii) incorporating an effective amount of a bio-based biocide composition comprising a) epoxidized 2-ethylhexyl soyate and b) solvent, leading to preserved polymer compositions as provided by the invention.

Preferred examples are halogenated polymers, more preferable is PVC.

With respect to their components, incorporation of the inventive bio-based biocide compositions into these polymers occurs separately, that is to say as individual components, in admixture, mixture, blend or pre-blend. For example, these can result from a pre-blending step. Incorporation can occur as addition, mixing, feeding, and the like.

In order that the invention disclosed herein may be more fully understood, the following examples are provided. These examples are for illustrative purposes only and are not to be construed as limiting the invention in any manner. As in the remainder of the description, parts and percentages are given based on weight unless stated otherwise.

EXAMPLES

Materials

The materials listed below were obtained from Galata Chemicals, LLC: epoxidized 2-ethylhexyl tallate (EOT) as Drapex® 4.4, epoxidized 2-ethylhexyl soyate (EOS) as Drapex® 5.2, epoxidized soybean oil (ESBO) as Drapex® 6.8. Di-isononyl phthalate (DINP) was received from Aldrich.

Examples 1

DINP, a conventional phthalate plasticizer was used as Control 1. A Control 2 was prepared by blending 50 g epoxidized 2-ethylhexyl tallate with 50 g epoxidized soybean oil. Bio-based biocide compositions of the invention were prepared by combining 50 g epoxidized 2-ethylhexyl soyate and 50 g epoxidized soybean oil (Sample 1). The respective blends were mixed for 1 hour at ambient temperature to obtain stable, homogeneous liquids.

Flexible Polyvinyl Chloride (PVC) Sample Preparation

The tested formulations included the following components: PVC resin Oxy-450 added at 100 phr; plasticizers: DINP added at 40 phr, a 50% solution of EOT in ESBO added at 40 phr, and a 50% solution of EOS in ESBO added at 40 and 36 phr; Ba/Zn stabilizer Mark® 4781A (marketed by Galata Chemicals LLC) and stearic acid lubricant were added to all formulations at 2.5 and 0.2 phr, respectively (Table 1).

The foregoing quantities are expressed in "phr", which stands for parts per 100 parts of PVC resin and indicates how many parts by weight of the particular substance are present in the PVC formulation based on 100 parts by weight PVC.

TABLE 1

Tested Formulations

| Components | Control 1 | Control 2 | I.E. A | I.E. B |
|---|---|---|---|---|
| PVC resin | 100 | 100 | 100 | 100 |
| Ba/Zn stabilizer | 2.5 | 2.5 | 2.5 | 2.5 |
| Stearic Acid | 0.2 | 0.2 | 0.2 | 0.2 |
| DINP | 40 | | | |
| EOT/ESBO | | 40 | | |
| EOS/ESBO | | | 40 | |
| EOS/ESBO | | | | 36 |

I.E.: Inventive Example

For the conversion of the powder form of the PVC formulations into a usable form, a sheet was prepared under standardized conditions using a two-roll mill (Dr. Collin GmbH, Ebersberg, Germany). The gap between the rolls was about 0.5 mm; temperature of the rolls 165° C.; time for preparation and homogenization: 5 minutes; sheet thickness 0.5 mm. The PVC sheet was continuously moved from the two sides to the center and the enlargement thus obtained was distributed over the gap with a wooden spatula over the roll with intensive homogenization of all components.

Testing of Plasticized Polyvinyl Chloride (PVC)

Example 2

Shore A Hardness

Shore A Hardness of the formulations was determined in accordance with ASTM D2240, using a commercially available Durometer Type A hardness tester (Shore Instrument & Mfg Co, Jamaica, N.Y., USA). The tested samples were prepared in accordance with the sample preparation technique described above. The results of the Shore A Hardness characterization were measured in triplicates, then averaged out and are shown in Table 2.

TABLE 2

Shore A Hardness

| Control 1 | Control 2 | I.E. A | I. E. B |
|---|---|---|---|
| 91 | 87 | 87 | 91 |

According to the results of table 2, Shore A Hardness of Control 1 is similar to that of I. E. B, and equal to 91, while Shore A Hardness of Control 2 is similar to that of I. E. A and equals 87.

Example 3

ASTM G21-96 (2009): Resistance of Synthetic Polymeric Materials to Fungi (Sections 6.4.1-6.4.7)

The specimens prepared under Example 1 were tested for their ability to resist contaminants when exposed to *Aspergillus brasiliensis* (formally known as *Aspergillus niger*, ATCC #9642), *Penicillium pinophilum* (ATCC #11797), *Chaetomium globosum* (ATCC #6205), *Gliocadium virens* (ATCC #9645) and *Aureobasidium pullulans* (ATCC #15233). Each material was exposed to each fungi in triplicate.

Specimen Preparation:

A sufficient amount of agar was poured into sterile containers. Once agar was solidified, specimens were placed on agar. Potato Dextrose Agar Petri dishes were inoculated with the spore suspension to serve as the viability control. The entire surface of the agar and specimens were inoculated with spore suspension with use of a sterilized atomizer. The test specimens were covered and incubated at 28 to 30° C. with a relative humidity of at least 85%. The specimens were periodically checked for growth during incubation. After 28 days the results were analyzed and a growth rating on the scale from 0 to 4 was given in accordance with ASTM G-21-96. The acceptance criterion was a no-growth-rating of higher than trace growth or a rating of 1. All samples receiving a growth rating of 2 or higher were considered failures.

| Observed Growth on Specimens (Sporulating or Non-Sporulating or Both) | Rating | Comments |
|---|---|---|
| None | 0 | Devoid of microbial growth. Surface exhibiting no chemical, physical or structural change. |
| Traces of Growth (less than 10%) | 1 | Scattered, sparse or very restricted microbial growth. Appearance on surface minor or inhibited. Surface exhibiting no chemical, physical or structural change. |
| Light Growth (10 to 30%) | 2 | Intermittent infestation. Loosely spread microbial colonies on surface moderate growth. Includes continuous filamentous (cobwebby) growth extending over the entire surface. Surface exhibiting no chemical, physical or structural change. |
| Medium Growth (30 to 60%) | 3 | Substantial amount of microbial growth. Surface exhibiting chemical, physical and structural change. |
| Heavy Growth (60% to complete coverage) | 4 | Massive microbial growth. Surface decomposed or rapidly deteriorating. |

The negative control used for the method showed no signs of growth. The positive control showed complete growth over the agar surface. The original number of fungus aerosolized onto the surface was $1.0 \times 10^8$ cfu/ml.

TABLE 2

Achieved microorganism-specific growth ratings

| Material | A. brasiliensis | A. pullulans | P. pinopino philum | G. virens | C. globosum | Average Rating for Resistance to Fungi | Percent Improvement of Resistance to Fungi compared with Control 1 |
|---|---|---|---|---|---|---|---|
| Control 1 | 1 | 1 | 1 | 1 | 1 | 1.7 | N/A |
| Control 1 | 2 | 2 | 2 | 2 | 2 | | |
| Control 1 | 2 | 2 | 2 | 2 | 2 | | |
| Control 2 | 2 | 2 | 2 | 2 | 2 | 3.0 | N/A |
| Control 2 | 3 | 3 | 3 | 3 | 3 | | |
| Control 2 | 4 | 4 | 4 | 4 | 4 | | |
| I. E. A | 1 | 1 | 1 | 1 | 1 | 1.3 | 24 |
| I. E. A | 2 | 2 | 2 | 2 | 2 | | |
| I. E. A | 1 | 1 | 1 | 1 | 1 | | |
| I. E. B | 1 | 1 | 1 | 1 | 1 | 1.0 | 41 |
| I. E. B | 1 | 1 | 1 | 1 | 1 | | |
| I. E. B | 1 | 1 | 1 | 1 | 1 | | |

Plasticizers are known to be a "food source" for microorganisms in PVC. It was surprisingly found that the PVC containing inventive examples function as effective biocides, as compared to the controls. Thus, the results showed that, at 36 phr, I. E. B, while also providing a Shore A Hardness of 91, met the acceptance criteria of ASTM G21-96 with all tested microbial contaminations (rating 1). Its average rating was 1.0 for three test runs As seen in Tables 1 and 2, at 40 phr I. E. A met the acceptance criteria of the ASTM G21-96 method with ratings of 1 and 2, respectively, while also giving a Shore A Hardness of 87. Its average resistance-to-fungi rating was 1.3 for three test runs.

DINP (Control 1, at 40 phr) gave an average rating for resistance to fungi of 1.7 with all microbial contaminations from three test runs. Its Shore A Hardness was observed to be 91.

As can be further seen from Table 2, Control 2 gave an average rating of 3.0 for resistance to fungi. By contrast, I.E. A and I.E. B gave superior average ratings of 1.3 and 1.0, respectively. Therefore, an average improvement in resistance-to-fungi for I.E. A and I.E. B over Control 1 was 0.4 and 0.7 average rating units or 24 and 41%, respectively.

EOS (which I.E. A and I. E. B comprise) is produced from soybean oil. By contrast, EOT (which Control 2 contains) is made from tall oil. EOS typically contains epoxidized 2-ethylhexyl linolenate, while EOT does not. Without wishing to be bound by any specific theory, it is believed that the unexpected and surprising difference in resistance to fungi seen between I.E. A and I.E. B on the one hand and Control 2 on the other is associated with said compositional difference.

What is claimed is:

1. A method of preserving a polymer comprising: combining a polymer and a bio-based biocide composition comprising epoxidized 2-ethylhexyl soyate and at least one solvent selected from the group consisting of esters, epoxidized esters, phthalates, alcohols, ketones, alkylpyrrolidones, alkyl phosphates and mixtures of at least two thereof, thereby forming a preserved polymer composition, the epoxidized 2-ethylhexyl soyate being present in the bio-based biocide composition in an amount from 20 to 90 weight percent based on the total weight of epoxidized 2-ethylhexyl soyate and solvent,
   wherein the bio-based biocide composition is present in an amount from 1 to 200 parts, based on 100 parts polymer.

2. The method of claim 1, wherein the preserved polymer composition exhibits resistance to fungi.

3. The method of claim 1, wherein the preserved polymer composition exhibits resistance to fungi as measured by test method ASTM G21-96.

4. The method of claim 3, wherein the preserved polymer composition exhibits improved resistance to fungi, as compared to the resistance to fungi of an otherwise identical composition except for the presence of the effective amount of a bio-based biocide composition.

5. The method of claim 4, wherein the resistance to fungi is improved by at least 15% as measured by test method ASTM G21-96.

6. The method of claim 4, wherein the resistance to fungi is improved by at least 30% as measured by test method ASTM G21-96.

7. The method of claim 4, wherein the resistance to fungi is improved by at least 40% as measured by test method ASTM G21-96.

8. The method of claim 1 comprising from about 5 to about 100 parts of the bio-based biocide composition, based on 100 parts of polymer.

9. The method of claim 8 comprising from about 10 to about 60 parts of the bio-based biocide composition, based on 100 parts of polymer.

10. The method of claim 9 comprising from about 30 to about 60 parts of the bio-based biocide composition, based on 100 parts of polymer.

11. The method of claim 3, wherein fungi is selected from the group consisting of *Aspergillus brasiliensis, Penicillium pinophilum, Chaetomium globosum, Gliocadium virens* and *Aureobasidium pullulans.*

12. The method of claim 1, wherein the at least one solvent is epoxidized soybean oil.

13. The method of claim 1 further comprising providing a conventional plasticizer selected from phthalates, hydrogenated phthalates, aliphatic esters of dicarboxylic acids, polymeric esters of dicarboxylic acids, citrates, sucrose esters, levulinic ketal esters, phosphates, alkyl phenol sulfonates, pyrrolidones, or mixtures of at least two thereof.

14. The method of claim 1 further comprising providing an additive.

15. The method of claim 14, wherein the additive is present and is selected from the group consisting of heat stabilizers, UV stabilizers and absorbers, antioxidants, lubricants, colorants, antistatic agents, and fillers.

16. The method of claim 15, wherein the heat stabilizer is alkali metal perchlorate.

17. The method of claim 16, wherein the alkali metal perchlorate is sodium perchlorate.

18. The method of claim 15, wherein the antioxidant is pentaerythritol tetrakis(3-(3,5-di-tert-butyl-4-hydroxyphenyl)propionate).

19. The method of claim 1, wherein the polymer is selected from the group consisting of PVC, PVC co-polymer, TPU, latex and wood-plastic composite.

20. The method of claim 1, wherein the polymer is or comprises PVC.

21. Polymer preserved by the method of claim 1.

22. A method of preserving a polymer comprising: combining a polymer and a bio-based biocide composition comprising epoxidized 2-ethylhexyl soyate and at least one solvent selected from the group consisting of esters, epoxidized esters, phthalates, alcohols, ketones, alkylpyrrolidones, alkyl phosphates and mixtures of at least two thereof, thereby forming a preserved polymer composition, the epoxidized 2-ethylhexyl soyate being present in the bio-based biocide composition in an amount from 40 to 60 weight percent based on the total weight of epoxidized 2-ethylhexyl soyate and solvent,
wherein the bio-based biocide composition is present in an amount from 1 to 200 parts, based on 100 parts polymer.

23. The method of claim 22 wherein the preserved polymer composition further comprises a microbiocide selected from 10,10'-oxybisphenoxarsine (OPBA), 4,5-dichloro-2-n-octyl-4-isothiazolin-3-one (DCOIT), 2-n-octyl-4-isothiazolin-3-one (OIT), n-butyl-1, 2-benzisothiazolin-3-one (BBIT), 2,4,4'-trichloro-2'-hydroxy-diphenyl-ether (TCPP), 3-iodo-2-propynyl butyl carbamate (IPBC), N-(tricholomethylthio phthalamide), zinc pyrithione (ZNP), 2-(4-thiazolyl)-benzimidazol (TBZ), carbendazim and 3-benzo[b]thien-2-yl-5,6-dihydro-1,4,2-oxathiazine 4-oxide, 2,3,5,6 tetrachloro 4 (methyl sulfanyl) pyridine, N-trichloromethylthio-4-cyclohexene-1,2-dicarboximide, octhilinone, pentachlorophenyl laurate, tetrachloroisophthalonitrile, silver-zinc zeolite, silver-copper zeolite, or mixtures of two or more thereof.

24. The method of claim 22, wherein the at least one solvent is epoxidized soybean oil.

* * * * *